United States Patent
Gekhter et al.

[11] Patent Number: 5,934,295
[45] Date of Patent: Aug. 10, 1999

[54] DENTAL HYGIENE SYSTEM

[75] Inventors: Vladamir Gekhter, Skokie; Leoncio Angel Gonzalez, Warrenville; Christopher J. Stvartak, Skokie; Mark D. Gleason, Buffalo Grove; David E. Hidding, Barrington; Kevin G. Yost, Winnetka, all of Ill.

[73] Assignee: John O. Butler Company, Chicago, Ill.

[21] Appl. No.: 09/057,195

[22] Filed: Apr. 8, 1998

[51] Int. Cl.⁶ ..................................................... A45D 44/18

[52] U.S. Cl. .......................................... 132/309; 433/146

[58] Field of Search ..................................... 132/309, 310, 132/321, 323, 324; 601/139, 141; 15/22.1, 167.1, 145, 176.1, 176.5, 176.6; 433/146, 147

[56] References Cited

U.S. PATENT DOCUMENTS

| | | | |
|---|---|---|---|
| 1,783,654 | 12/1930 | Kelsey | 433/147 |
| 4,974,286 | 12/1990 | Stowell et al. | 16/111 |
| 5,058,230 | 10/1991 | Hodosh et al. | 15/167.1 |
| 5,398,369 | 3/1995 | Heinzelman et al. | 15/167.1 |
| 5,511,276 | 4/1996 | Lee | 15/167.1 |
| 5,581,838 | 12/1996 | Rocco | 132/309 |

*Primary Examiner*—John J. Wilson
*Attorney, Agent, or Firm*—Laff, Whitesel & Saret, Ltd.

[57] ABSTRACT

A dental hygiene system in which a single elongated handle having a recess in its distal end receives a plurality of carrying members holding different dental hygiene elements. The carrying members have resilient portions retained in the handle recess by way of either a latching portion in a slot in the handle or by way of a frictional fit in the handle recess. A lever is positioned in the slot in the handle for releasing the carrying members with the latching portion.

9 Claims, 5 Drawing Sheets

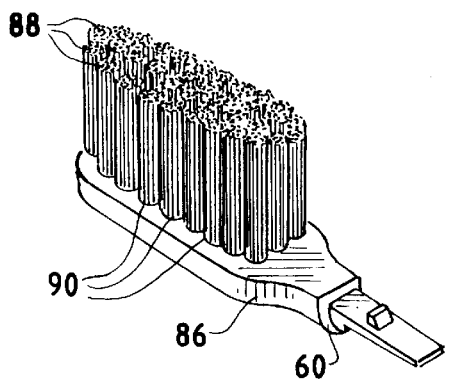
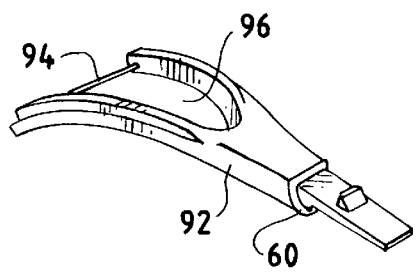
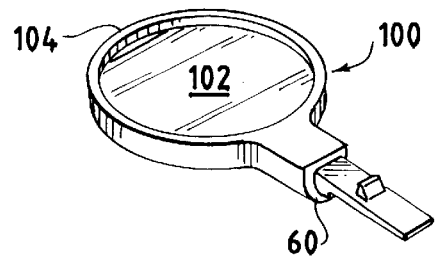
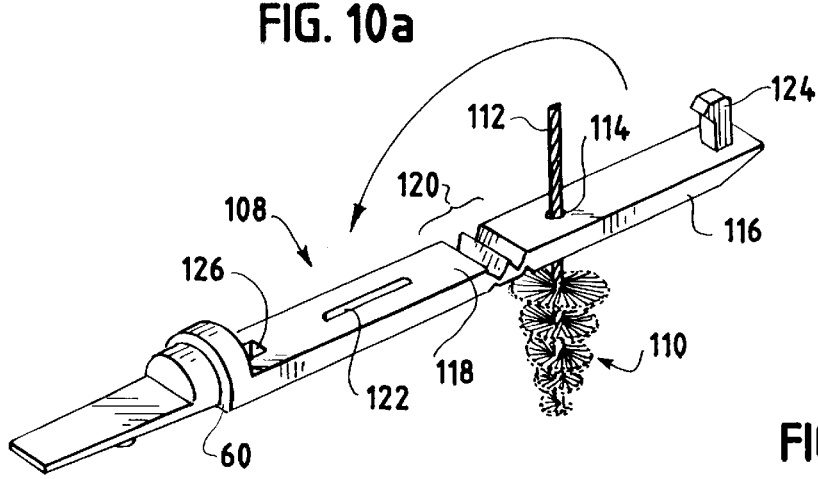
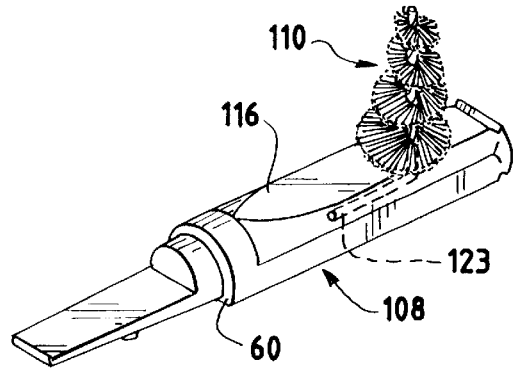

DENTAL HYGIENE SYSTEM

FIELD OF THE INVENTION

The present invention relates generally to dental hygiene systems intended for manual operation and more particularly to an improved dental hygiene system in which a single handle accepts a series of different dental cleaning or stimulating elements mounted in convenient carrying members which are easily attached and removed from the handle.

BACKGROUND OF THE INVENTION

Various devices are known in the art for cleaning and stimulating the teeth and gums to maintain good dental hygiene. The most ubiquitous such device is the conventional toothbrush. Another popular cleaning and stimulating device is an interproximal toothbrush such as one of the many different interproximal toothbrushes which are available from John O. Butler Company of Chicago, Ill. Still other types of commonly used cleaning and stimulating devices are rubber stimulators, picks, flossers and even small dental mirrors which aid in monitoring inaccessible areas in the mouth.

Typically, these cleaning and stimulating devices are single units comprising a handle and a brush or other cleaning or stimulating element. Anyone wishing to partake of two or more of these tooth cleaning or stimulating devices must undertake the expense of purchasing, and the inconvenience of storing two or more different unitary devices. Also, as the cleaning or stimulating elements wear out, the entire device (unitary handle and element) must be discarded and replaced. This expense and inconvenience discourages most people from using and maintaining more than a simple unitary toothbrush. As a result, most people achieve less than optimal dental hygiene.

While most toothbrushes are of a single-piece construction, two-piece toothbrushes have also been available in the marketplace from time-to-time. These two-piece toothbrushes, in which a handle and small removable brush element are typically provided, have not fully satisfied the needs and desires of many users. This has been primarily due to difficulties in handling the small brush element and the inconvenience of attaching and detaching the handle and the removable brush element. It has also been due to the relatively insecure attachment achieved in such devices, particularly after mechanisms used to secure the brush to the handle are subjected to wear over an extended period of time.

It is therefore an object of the present invention to provide a dental hygiene mechanism in which a series of different dental cleaning and stimulating elements can be attached to a single handle, thereby alleviating the need to purchase or maintain multiple unitary dental hygiene devices.

Another object of the present invention is to provide a dental hygiene system having an improved locking system in which a variety of different cleaning and stimulating elements can be easily and reliably attached and detached from a single handle.

Yet another object of the invention is to provide a dental hygiene system including a handle and a variety of different cleaning and stimulating elements in which the handle will withstand repeated changes of the elements without significant wear.

A further object of the invention is to provide a dental hygiene system including a handle and a variety of different cleaning and stimulating elements in which the cleaning and stimulating elements are mounted in carrying members which are easy to handle and convenient to use.

These and other objects and advantages of the invention will appear hereinafter.

SUMMARY OF THE INVENTION

The present invention, in a preferred embodiment, accomplishes the foregoing objects by providing a dental hygiene system comprising an elongated handle with a proximal gripping section and a distal attachment section. The attachment section of the handle has a recess opening into an aperture in the distal end of the handle for receiving a carrying member, as described below. The attachment section of the handle also has a top surface with a slot which opens into the recess.

A plurality of carrying members for holding different dental hygiene elements are provided in the dental hygiene system of the invention. The carrying members have resilient engagement portions which are intended to be inserted in the handle recess. In at least some of the carrying members, the engagement portions include a resilient member carrying means for latching in the handle slot. Other carrying members may include a solid engagement portion which is slightly larger than the recess and is compressed when the carrying member is attached to the handle. In this case the carrying member is held in place by way of the friction between the solid engagement portion and the walls of the handle recess.

A release lever is positioned in the slot in the handle, with its top surface protruding above the top surface of the slot. The bottom of the release lever is coplanar with the surface of the recess. When the user wishes to change a carrying member with the wedge latching system, he or she simply presses down upon the release lever which moves the wedge out of engagement with the handle slot so that the carrying member can be easily withdrawn from the handle recess. Alternatively, when the user wishes to change a carrying member with the solid engagement portion, he or she can just pull on the carrying member hard enough to overcome the frictional grip of the engagement portion in the handle recess.

A variety of different cleaning and stimulating elements can be mounted in the carrying members. These include but are not limited to fixed interproximal brushes, removable interdental brushes, stimulating elements, picks, single tuft toothbrushes, multi-tuft toothbrushes, flossers and mirrors.

The above as well as other objects and advantages of the invention will become apparent from the following detailed description of the preferred embodiments in which reference is made to the accompanying drawings.

BRIEF DESCRIPTION OF THE DRAWINGS

FIG. 9f is a perspective view of a carrying member in accordance with FIG. 5 in which a conventional toothbrush is mounted in the distal end of the carrying member;

FIG. 9g is a perspective view of a carrying member in accordance with FIG. 5 in which a flosser is mounted in the distal end of the carrying member;

FIG. 9h is a perspective view of a carrying member in accordance with FIG. 5 in which a mirror is mounted in the distal end of the carrying member;

FIG. 10a is a perspective view an alternate embodiment of FIG. 9a in which the carrying member comprises an interdental brush holder and a replaceable interdental brush is shown being inserted into the holder; and FIG. 10b is a perspective view the interdental toothbrush holder of FIG. 10a in its closed position, with a twisted wire of the interdental brush locked in place in the holder.

DETAILED DESCRIPTION OF A PREFERRED EMBODIMENT

Figure 1:
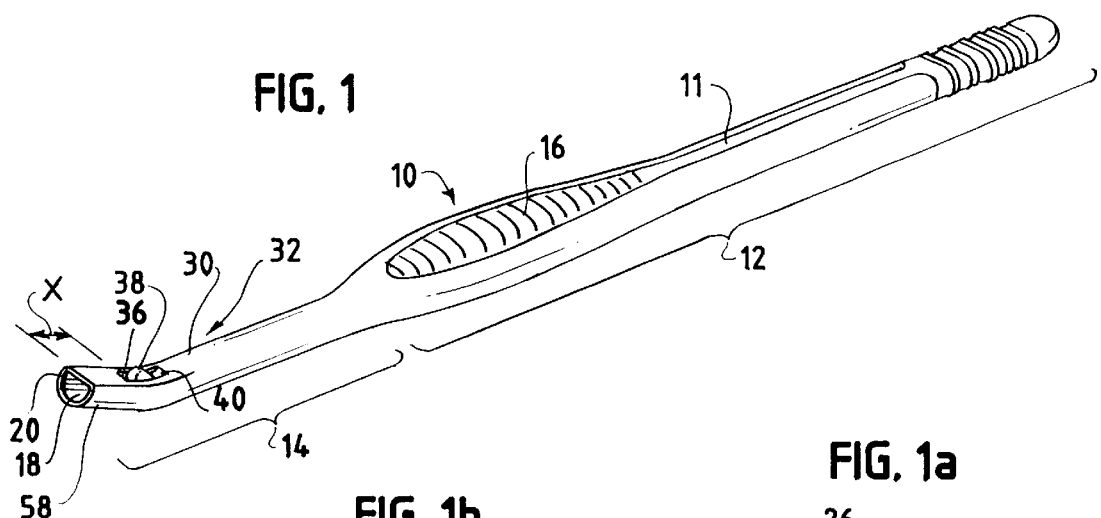
FIG. 1 is a perspective view of an elongated universal handle intended to be used in the dental system of the present invention.

Referring now to the drawings, where like reference numerals have been used to designate like or similar elements, there is shown in FIG. 1, an elongated universal handle 10 having a hand gripping section 12 at its proximal end and an attachment section 14 at its distal end. Since a single universal handle is used in the dental hygiene system of the invention with a variety of replaceable carrying members, it is practically possible to invest more in the construction of the handle than is possible in unitary dental hygiene devices. Thus, elongated universal handle 10 has soft elastomer over-molded areas 11 to give the handle improved comfort and aesthetics while providing an optimum grip. It is preferred that the elastomer have a Shore A hardness of less than about 60. Hand gripping section 12 is wider across its face 16 than it is thick to help the user orient the handle in his or her hand.

Handle 10 may be made by injection molding a thermoplastic which is flexible yet durable enough to support the release lever discussed below. Such thermoplastics include polypropylene, polyester or nylon. Most preferably the handle is made of polypropylene. Alternatively, the handle may be made of metal such as a stainless steel having the appropriate flex modulus.

Figure 1A:
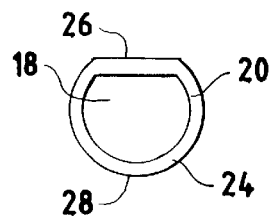
FIG. 1a is an enlarged end view of the handle of FIG. 1.

Attachment section 14 includes a recess 18 which opens into the distal end of the handle at aperture 20. Recess 18 extends proximally into the handle to a proximal wall 19 (FIG. 4) which defines the depth of the recess. Aperture 20, which is seen in cross-section in FIG. 1a, is defined by a thin wall 22 (FIG. 4) which surrounds the recess. Wall 22 is generally perpendicular to the planar face 24 of aperture 20.

The D-shaped configuration of recess 18 is an important feature of the invention. It includes a flat top portion 26 which is generally parallel to face 16 of the handle, and a rounded or circular bottom portion 28. As explained below, the flat top portion and circular bottom portion help insure that the carrying member is mounted properly in the universal handle.

Figure 1B:
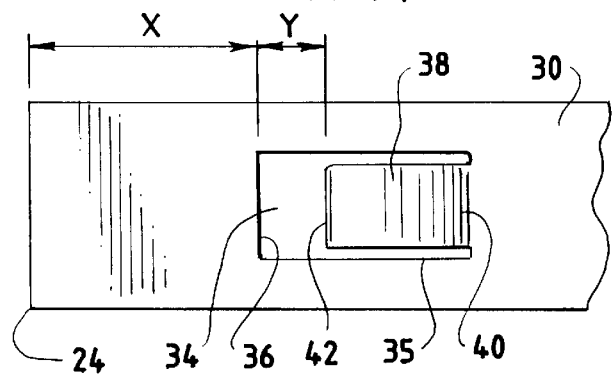
FIG. 1b is an enlarged plan view of a slot in the handle of FIG. 1 in which a release lever is provided in accordance with the invention for detaching carrying members.

Attachment section 14 includes a flat surface 30 which extends from the neck 32 of the handle to its distal end. As shown in FIG. 1, neck 32 curves gently upwardly from the plane of face 16. A rectangular slot 34 (FIG. 1b) having its longer side 35 parallel to the longitudinal axis of the handle is formed in the flat surface 30, in communication with recess 18. The flat distal edge 36 of slot 34 is spaced a predetermined distance "x" from planar face 24 of aperture 20.

Figure 4:
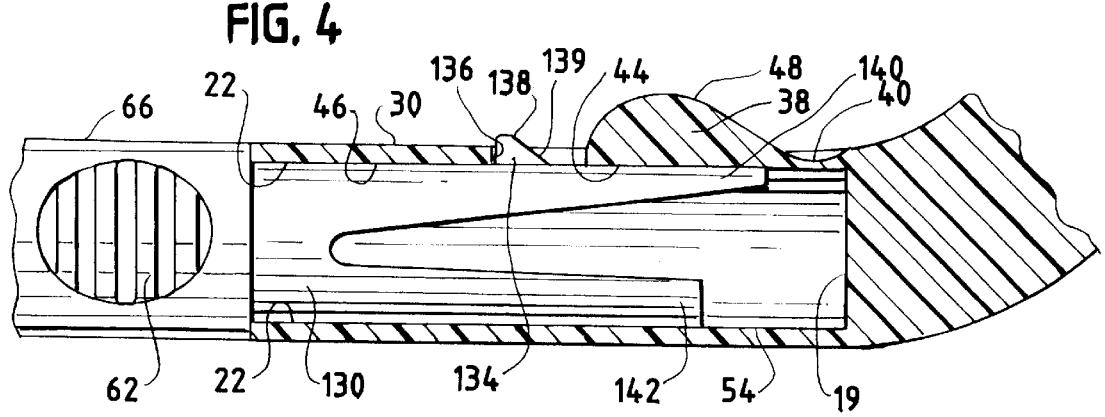
FIG. 4 is an enlarged cutaway view of the handle FIG. 1 showing the carrying member of FIG. 2 in fully latched position in the handle of FIG. 1.

A release lever 38 is molded into the handle such that it is attached along a web 40 at its base and otherwise free of slot 34. The distal edge 42 of release lever 38 is spaced a predetermined distance "y" from the distal edge 36 of slot 34. As best seen in FIG. 4, release lever 38 includes a flat underside 44 which is co-planer with the underside 46 of wall 22 of recess 18. The top surface 48 of release lever 38, curves gently upward from web 40 so that it protrudes above the flat surface 30 of the handle.

Figure 2:
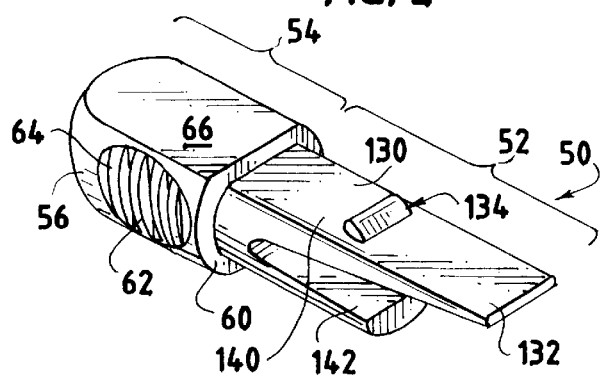
FIG. 2 is an enlarged perspective view of a carrying member intended to be inserted into the handle of FIG. 1.

A preferred carrying member 50 is illustrated in FIG. 2. Although carrying member 50 may be made of the same material as handle 10, it need not be made of a material as durable as that of the handle since the carrying members are intended to be replaced and therefore to absorb the wear, if any, which occurs on insertion and removal from the handle. Therefore, it is preferred that the carrying members be made of a material having a resistance to deformation and fatigue less than that of the handle, so that the carrying members absorb more of the wear than the handle.

Carrying member 50 includes an engagement portion 52 and a holder portion 54. Holder portion 54 is generally of a D-shaped cross-section corresponding in shape to recess 18 and having an outer surface 56 generally corresponding to the outer surface 58 of wall 22 so that when attached, the handle and carrying member present a smooth surface from the gripping end of the handle through the cleaning or stimulating element at the distal end of the device. Engagement portion 52 has a collar 130, as described in more detail below, with a corresponding shape, which is stepped down in size a distance corresponding to the thickness of wall 22 which surrounds recess 18 so that it corresponds to the size and shape of recess 18 and can be inserted therein. As a result, a shoulder 60 is formed at the point of transition between the engagement and holder portions. Shoulder 60 is generally perpendicular to the outer surfaces of the engagement and holder portions.

Additionally, generally circular indentations 62 are formed on either side of the carrying member with a series of ribs 64 generally perpendicular to the flat top surface 66 of the engagement portion within the indentations. The indentations and ribs assist the user in handling the carrying member and in orienting it with respect to the aperture 18 in the handle by providing a visual and tactile point of reference as the user picks up and orients the relatively small carrying member, typically between the pads of the thumb and forefinger. Top flat surface 66 further assists the user by providing a visual reference for aligning the carrying member with respect to the top flat portion 26 of recess 18.

Figure 9A:
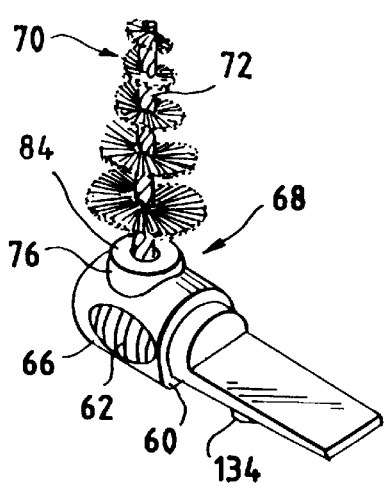
FIG. 9a is a perspective view of a carrying member in accordance with FIG. 5 in which an interdental brush is permanently mounted in the distal end of the carrying member.

A dental hygiene element in the form of a cleaning or stimulating element will typically protrude from the bottom 68 of the carrying member (see FIGS. 9a–9c), although it may protrude from flat top surface 66 (FIG.2). These elements may be molded or mounted into the carrying member by known techniques. Thus, for example, as shown in FIG. 9a, an interdental brush 70 is illustrated with its central twisted wire portion 72 permanently secured into a pedestal 76 in the bottom of the carrying member.

Figure 9B:
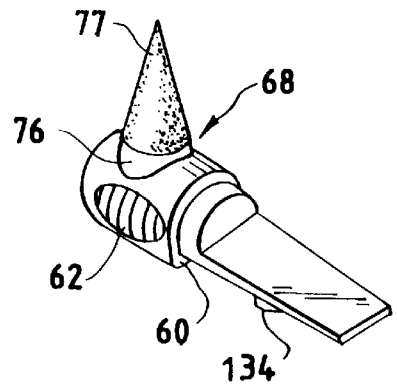
FIG. 9b is a perspective view of a carrying member in accordance with FIG. 5 in which a stimulator is mounted in the distal end of the carrying member.
Figure 9C:
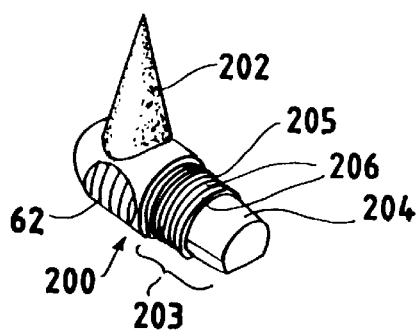
FIG. 9c is an alternate embodiment of the carrying member with stimulator of FIG. 9b.

In FIG. 9b, conical element 77 is shown mounted into pedestal 76 which protrudes from the bottom 68 of the carrying member. This conical element may be made of an elastomer and function as a gum stimulator for massaging the gums. It may be a separate piece, as indicated in FIG. 9b, mounted in the carrying member by conventional means. Alternatively, a carrying member 200 with an integral gum stimulator 202 may be molded of a single piece of an elastomer, as illustrated in FIG. 9c. In this case, a "D" shaped solid engagement portion 203 is provided, shaped to follow the contours of recess 18. Solid engagement portion 203 includes a pilot section 204 which is slightly smaller than the recess to aid the user in placing the engagement section in the recess. Engagement portion 204 also includes a retention section 205 comprising a series of ribs 206. Retention section 205 is slightly larger than the recess so that some resistance is encountered as the retention section enters the recess. Therefore, as the user presses the engagement portion into the recess, the ribs are compressed and a snug grip is achieved between the elastomer ribs 206 and the more rigid walls 22 which define recess 18 to resist unintended pull-out of carrying member 200.

Figure 9D:
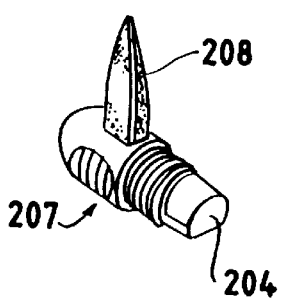
FIG. 9d is a perspective view of a carrying member in accordance with FIG. 5 in which a pick is mounted in the distal end of the carrying member.

Carrying members with other elements can, of course, use such a frictional engagement system as well. For example, FIG. 9d illustrates a carrying member 207 with a flattened conical element 208 made of polypropylene and shaped to serve as a pick for removing debris from between the teeth and below the gum line. Although in this case the carrying member and pick are molded as a single piece and intended to be held in place in the universal handle by friction, two-piece construction as in FIG. 9b is also contemplated for this member.

Figure 9E:
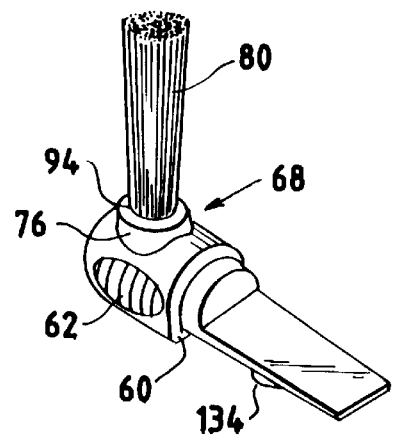
FIG. 9e is a perspective view of a carrying member in accordance with FIG. 5 in which a single tuft brush is mounted in the distal end of the carrying member.

In FIG. 9e, yet another carrying member is illustrated in which a single tuft of bristles 80 is mounted into a preformed aperture 84 in the pedestal 76 of carrying member by conventional means. This tuft may be used for both cleaning and stimulating the teeth and gums.

In FIG. 9f, the design of the previous carrying members is substantially reconfigured to provide a generally flat base 86 large enough to hold a series of tufts of bristles 88, as in a conventional multi-tuft toothbrush head. Shoulder 60 and collar 130 (discussed below) are maintained in this design. The tufts are mounted in preformed holes 90 in the carrying member using conventional means.

A flosser or dental floss handle 92 is shown in FIG. 9g with floss 94 mounted tautly across the opening 96 of the dental floss holder. The dental floss holder is oriented so that when the carrying member is mounted in the handle the dental floss lies in a plane parallel to face 16 of the handle.

Finally, in FIG. 9h, a mirror 100 is shown in the holder portion of the carrying member. This includes a reflective element 102 which is held in place by 10 conventional means in a collar 104.

In an alternate embodiment of the carrying member with interdental brush of FIG. 9a, an interdental brushholder 108 and replaceable interdental brush 110 are shown in FIGS. 10a and 10b. This interdental brush holder corresponds generally to the teaching of John O. Butler Company's U.S. Pat. Nos. 5,027,467; 5,201,091; and 5,347,675. In FIG. 10a, holder 108 is in an open position with the protruding central twisted wire portion 112 of interdental brush 110 inserted into a hole 114 in the cover 116 of the holder. This cover is attached to a base portion 118 by living hinges 120. With the interdental brush in this preloaded position, cover 116 is rotated 180 degrees as the twisted wire portion 112 engages a slot 122 in the base portion and is bent into a generally L-shaped configuration 123. When the cover is fully closed, latch 124 engages an aperture 126, to lock the interdental brush in place. When this interdental brush is spent, it may be replaced by releasing latch 124, removing the brush and inserting a fresh brush in the same manner.

Returning now to the engagement portion of the carrying member, several variations of a preferred fundamental design structure are shown. In all of the structures, a collar 130 adjacent shoulder 60, a generally flat longitudinally oriented surface 132 extending from the collar, and latching means protruding from the flat surface are provided. The collar and the flat surface are perpendicular to shoulder 60 of the carrying member. Collar 130, generally flat longitudinally oriented surface 132, and preferred latching means in the form of a wedge 134 are shown, for example, in the carrying member of FIG. 2 with wedge 134 is oriented generally perpendicularly to the longitudinal axis of the carrying member and generally parallel to shoulder 60.

Wedge 134 includes a front surface 136 parallel to shoulder 60, a top flat surface 138 as well as a ramp surface 139 along its back edge. Front surface 136 of the wedge is spaced from shoulder 60 a distance corresponding to the spacing "x" between the flat distal edge 36 of the slot and planar face 24 of aperture 20 in the handle. As a result, as explained below, when the engagement portion of the carrying member is fully inserted in recess 18, the front surface of the wedge will just clear edge 36 of slot 34. The width of the wedge is just slightly less than the width of slot 34 and its length is slightly less than the distance "y" between the distal edge 42 of release lever 38 and the distal edge 36 of aperture 34. This makes for secure, wobble-free retention of the carrying member in the handle.

Figure 3:
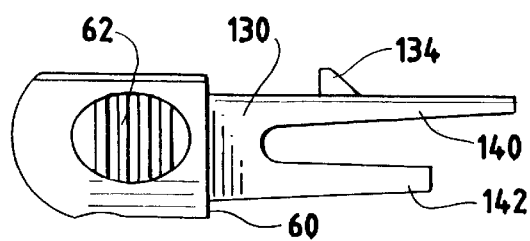
FIG. 3 is an elevation view of the carrying member of FIG. 2.

In the carrying member of FIGS. 2, 3, and 4, the engagement portion includes a top leg 140 and a shorter bottom leg 142. In the carrying member of FIG. 5, the bottom leg is eliminated. FIGS. 6 and 7 illustrate other alternate configurations of the engagement portion of the carrying member. In all of these embodiments, the carrying portion operates generally in the same manner, notwithstanding that in the configuration of FIG. 5 there is no flexure in the remaining top leg of the engagement portion until collar 130 engages recess 18. In all of these embodiments, a firm mounting of the carrying member in the handle is achieved by making the "D" shaped profile of the engagement portion correspond to the profile of recess 18 and the width of the engagement portion slightly larger than the width of the recess.

In the configuration of FIG. 6, the engagement portion comprises a single offset leg 144, including an upwardly projecting portion 146 where it protrudes from the collar 130 of the engagement portion, a top horizontal portion 148 and a downwardly directed rear rounded tail 150. Offset leg 144 has a generally uniform cross-section along its length, as illustrated in FIGS. 6a, 6b and 6c. These figures represent alternative cross-sectional profiles taken along line 6a—6a in FIG. 6, including a rectangular configuration 147 having rounded corners 149, an oval configuration 151, and a plain rectangular configuration 153. When a is carrying member with offset leg 144 is inserted into the recess in the handle, the top surface of the top horizontal portion 148 engages the underside 46 of the recess (FIG. 4) while the rounded bottom edge 152 of the tail engages the bottom surface 54 of the recess.

FIG. 7 illustrates yet a further configuration of the engagement portion of the holding member. In this configuration, a curved top leg 156 and a curved bottom leg 158 come together to form a "bow" resiliently attached at one end to collar 130 and resiliently attached to each other at the opposite end 160. The top and bottom legs flex inwardly when pressure is applied generally perpendicularly to the longitudinal axis of the "bow". The top and bottom legs will have uniform cross-sections, for example as illustrated in FIGS. 7a and 7b. In both of these figures, the top and bottom legs are shown at they would look at rest in cavity 18, with a cross-section taken across the "bow" at line 7b—7b in FIG. 7. In the configuration of FIG. 7a, which is preferred, the legs are contoured to correspond to the shape of cavity 18 and to meet the surface of the cavity along the entirety of their outer surfaces. In the configuration of FIG. 7b, the contours of the legs are more rounded, so that there is less contact with the surface of the cavity.

Insertion and removal of a carrying member of FIG. 2 is shown in FIGS. 8a–8e. Thus, in FIG. 8a, carrying member 50 has been oriented by the user (gripping at indentations 62 on either side of the carrying member) so that both top surface 66 of holder portion 54 and flat top surface 132 of top leg 140 of the engagement portion 52 of the carrying member are aligned with the flat top surface of recess 18 while the bottom curved surface of the attachment section rests in the circular bottom portion of the recess. The forward portion of legs 140 and 142 are shown inserted in the aperture, just short of wedge 134. In this embodiment, the legs are angled apart approximately, (for example about 2–5°) so that when the legs are inserted as in FIG. 8a they squeeze together slightly to make for a firm initial grip.

Figure 8A:
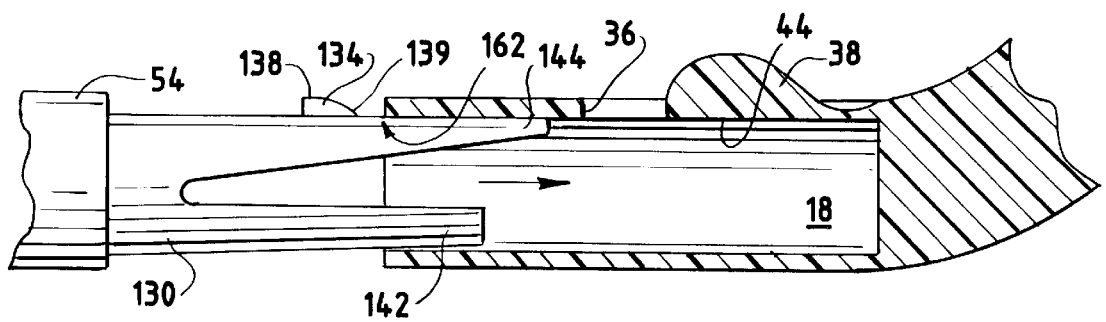
FIGS. 8a–8e comprise a series of cutaway enlarged side elevation views illustrating the engagement and disengagement of the carrying member of FIG. 2 and the handle of FIG. 1.
Figure 8B:
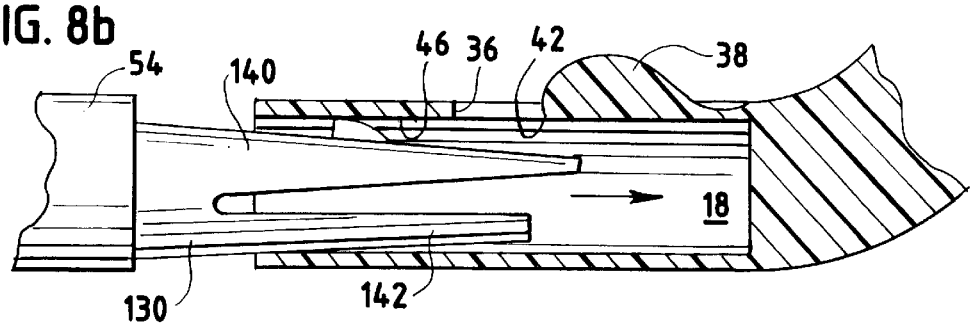
Figure 8C:
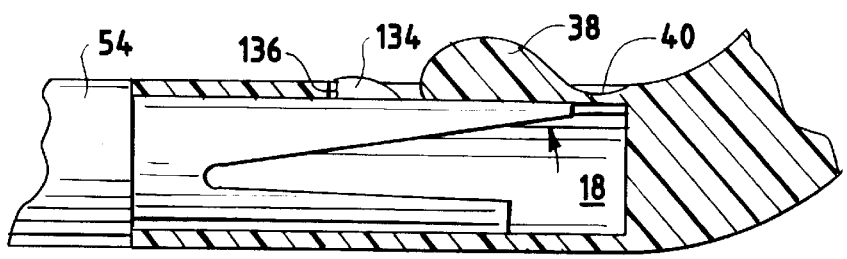

As insertion proceeds, ramp 139 of wedge 134 engages the leading edge 162 of recess 18, squeezing together legs 140 and 142 as shown in FIG. 8b so that the wedge enters the recess with its top flat surface 138 gliding along the underside 46 of wall 22 of recess 18. Insertion continues until collar 130 enters the recess and shoulder 60 meets planar face 24 of aperture 20, coinciding with entry by the wedge into slot 34. As the wedge enters slot 34, as shown in FIG. 8c, the tension on legs 140 and 142 due to the interference between the wedge and the wall of the recess is relieved and the carrying member is locked in place by virtue of the cooperation between shoulder 60 against planar face 24 of aperture 20 and front surface 136 of the wedge against edge 36 of slot 34. As can be seen in this figure, release lever 38 is unaffected since top leg 140 of the engagement portion of the carrying member simply rests adjacent bottom surface 44 of the release lever, free of any stresses. This normal resting position of the release lever free of stresses is an important feature of the invention since it makes for a more reliable, long-lived release mechanism in a universal handle which is intended to be used over an extended period of time with a series of different carrying members.

Figure 8D:
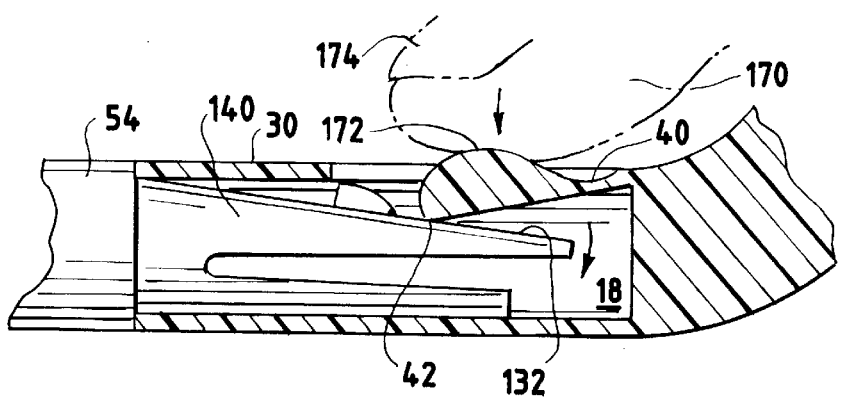

When it is desired to release the carrying member from the handle, the user grasps the handles and presses with a thumb 170, as illustrated in FIG. 8d. Users may prefer at this point to use either the pad of the thumb 172, as illustrated, or the fingernail 174. Thus, as the user presses down upon release lever 38 which flexes across web 40, the forward edge 42 of the release lever engages the top flat surface 132 of top leg 140 of the engagement portion to squeeze the top leg downwardly until the wedge clears the edge 36 of slot 34 in the handle.

Figure 8E:
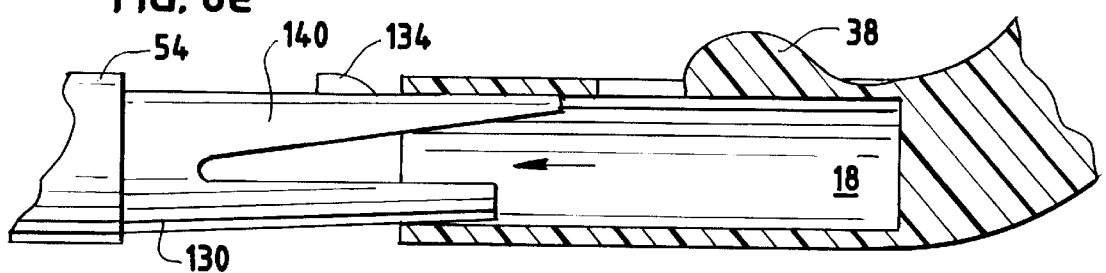

Meanwhile, the user, with the other hand, grasps the carrying member across indentations 62, as discussed earlier, and pulls upon the carrying member to slide it out of the recess as the wedge clears slot 34, as shown in FIGS. 8d and 8e. A new carrying member can then be inserted as illustrated in FIGS. 8a–8c.

Figure 5:
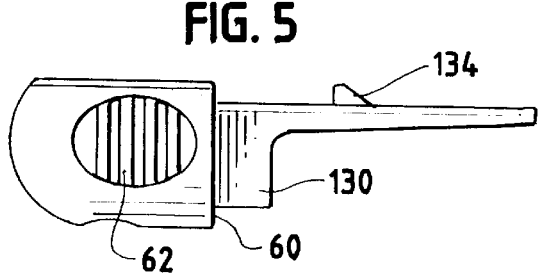
FIG. 5 is an elevation view of a carrying member with an alternate engagement configuration utilizing an offset leg shape.
Figure 6:
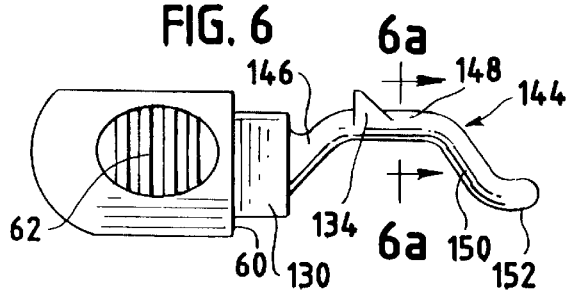
FIG. 6 is an elevation view of a carrying member with another alternative engagement configuration.
Figure 6A:
FIGS. 6a–6c are alternate cross-sectional views, taken along line 6a—6a of FIG. 6, of the offset leg of FIG. 6.
Figure 6B:
Figure 6C:
Figure 7:
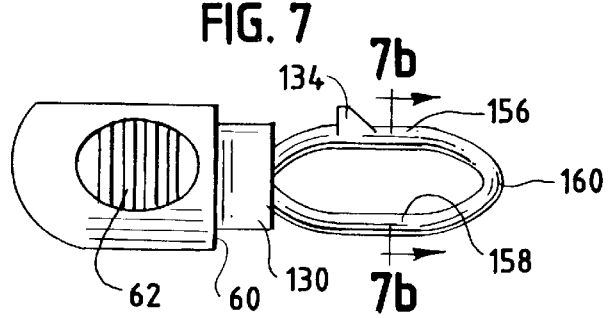
FIG. 7 is an elevation view of a carrying member with yet another engagement configuration utilizing a bow leg shape.
Figure 7A:
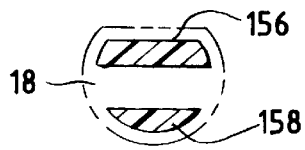
FIGS. 7a and 7b are alternate cross sectional views taken along line 7b—7b of FIG. 7 showing the bow leg shape as it rests within the handle of FIG. 1.
Figure 7B:
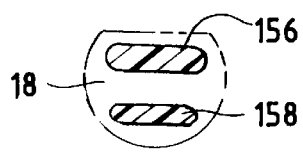

Insertion and release of the carrying members for each of the designs of FIGS. 5, 6 and 7 proceeds generally as described above. For example, in the case of the offset leg design of FIG. 7, as the engagement portion is inserted into recess 18, ramp 139 of wedge 134 meets the leading edge 162 of recess 18, as illustrated with regard to the double leg attachment section design in FIG. 8a and, as it is advanced into the cavity, the "bow" is squeezed together in much the same way as the two legs of the attachment section are flexed together, as illustrated in FIG. 8b. (Ramp 139 is shown in FIGS. 8a–8e as a gently curving surface.) As can readily be appreciated, the rest of the insertion and removal process also proceeds as in remaining FIGS. 8c–8e. In the case of the offset leg (FIG. 6) and single leg (FIG. 5) designs, flexure of the legs is delayed until collar 130 enters the cavity to resist rotation of the engagement portion, forcing the legs to bend to accommodate the wedge riding along the top surface 46 of cavity 18.

While the present invention is described above in connection with specific embodiments, the invention is intended to cover all alternatives, modifications or equivalents that may be included within its sphere and scope, as defined by the appended claims

What we claim is:

1. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement potions for attachment to the handle;

at least some of the carrying members including elastomeric engagement portions which hold the carrying members in the recess of the handle;

the engagement portions of at least some of the carrying members having a resilient member carrying means for latching in the slot to hold the carrying members in the handle of the recess; and a release lever positioned in the slot of the handle so that pressure applied to the release lever will move the latching means clear of the slot so that carrying members can be removed from the recess.

2. A dental hygiene system as in claim 1 in which the carrying members are made of a material having a resistance to deformation and fatigue less than that of the handle so that the carrying members absorb more of the wear than the handle as different carrying members are removed and inserted in the handle.

3. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement potions for attachment to the handle;

the engagement portions of the carrying members and the recess of the handle having corresponding D-shaped configurations;

at least some of the carrying members having elastomeric engagement portions which hold the carrying members in the recess of the handle;

the elastomeric engagement portions including ribs which are compressed when the carrying members are inserted in the recess of the handle;

the engagement portions of at least some of the carrying members having a resilient member carrying means for latching in the slot to hold the carrying members in the handle of the recess; and a release lever positioned in the slot of the handle so that pressure applied to the release lever will move the latching means clear of the slot so that carrying members can be removed from the recess.

4. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement potions for attachment to the handle;

the carrying members including holder portions for dental hygiene elements and at least two indentations in opposite sides of the holder portions to assist the user in handling the carrying members;

the engagement portions of at least some of the carrying members having a resilient member carrying means for latching in the slot to hold the carrying members in the handle of the recess; and a release lever positioned in the slot of the handle so that pressure applied to the release lever will move the latching means clear of the slot so that carrying members can be removed from the recess.

5. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement potions for attachment to the handle;

the carrying members including holder portions for dental hygiene elements with at least two indentations in opposite of the holder portions to assist the user in handling the carrying members, wherein ribs are formed in the indentations;

the engagement portions of at least some of the carrying members having a resilient member carrying means for latching in the slot to hold the carrying members in the handle of the recess; and a release lever positioned in the slot of the handle so that pressure applied to the release lever will move the latching means clear of the slot so that carrying members can be removed from the recess.

6. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement potions for attachment to the handle;

the engagement portions of at least some of the carrying members having a resilient member carrying means for latching in the slot to hold the carrying members in the handle of the recess;

the latching means comprising a wedge;

the resilient member comprising a pair of longitudinal legs and the wedge projecting upwardly from one of the legs; and a release lever positioned in the slot of the handle so that pressure applied to the release lever will move the latching means clear of the slot so that carrying members can be removed from the recess.

7. A dental hygiene comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement portions for attachment to the handle;

the engagement portions of at least some of the carrying members having a resilient member carrying means for latching in the slot to hold the carrying members in the handle of the recess;

the resilient member comprising curved top and bottom legs which are joined to form a bow; and a release lever positioned in the slot of the handle so that pressure applied to the release lever will move the latching means clear of the slot so that carrying members can be removed from the recess.

8. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement portions for attachment to the handle;

the engagement portions of at least some of the carrying members having a resilient member carrying means for latching in the slot to hold the carrying members in the handle of the recess; and a release lever positioned in the slot of the handle so that the release lever protrudes above the top surface of the attachment section of the handle but does not extend into the handle until it is pressed, the pressure moving the latching means clear of the slot so that carrying members can be removed from the recess.

9. A dental hygiene system comprising:

an elongated handle having a proximal gripping section and a distal attachment section;

the attachment section having a distal end and a recess opening into an aperture in the distal end;

the attachment section also having a top surface and a slot formed in the top surface, in communication with the recess;

a plurality of members for carrying dental hygiene elements, the carrying members each having engagement portions for attachment to the handle;

the engagement portions of at least some of the carrying members having a resilient member carrying a wedge for latching in the slot to hold the carrying members in the handle recess;

the engagement portions of at least some of the carrying members include elastomeric engagement portions for holding the carrying members in the recess in the handle by friction; and a release lever positioned in the slot of the handle so that pressure applied to the release lever will move the wedge clear of the slot so that the carrying members having a resilient member carrying a wedge can be removed from the recess.

* * * * *